(12) United States Patent
Bates

(10) Patent No.: US 8,313,495 B2
(45) Date of Patent: Nov. 20, 2012

(54) NEEDLE HOLDER AND SUTURE CUTTER SURGICAL INSTRUMENT

(76) Inventor: James E Bates, San Diego, CA (US)

( * ) Notice: Subject to any disclaimer, the term of this patent is extended or adjusted under 35 U.S.C. 154(b) by 173 days.

(21) Appl. No.: 12/839,275

(22) Filed: Jul. 19, 2010

(65) Prior Publication Data

US 2012/0016382 A1    Jan. 19, 2012

(51) Int. Cl.
*A61B 17/10*    (2006.01)
(52) U.S. Cl. .............. 606/138; 606/148; 30/194
(58) Field of Classification Search .......... 606/138–139, 606/144, 147–148, 157, 167, 174–175; 30/146, 30/155, 194, 208; 112/125, 129, 130
See application file for complete search history.

(56) References Cited

U.S. PATENT DOCUMENTS

| | | | |
|---|---|---|---|
| 1,579,379 A | 4/1926 | Marbel | |
| 2,778,254 A * | 1/1957 | Carapellotti | ................... 81/3.56 |
| 2,998,649 A | 9/1961 | Miller et al. | |
| 3,443,313 A | 5/1969 | Profy | |
| 3,576,072 A | 4/1971 | Foster | |
| 3,802,074 A | 4/1974 | Hoppe | |
| 4,271,838 A | 6/1981 | Lasner et al. | |
| 4,452,246 A | 6/1984 | Bader et al. | |
| 4,658,456 A * | 4/1987 | Tsai | ................... 7/135 |
| 4,669,470 A | 6/1987 | Brandfield | |
| 5,015,252 A | 5/1991 | Jones | |
| 5,196,023 A | 3/1993 | Martin | |
| 5,346,500 A | 9/1994 | Suchart | |
| 5,439,471 A | 8/1995 | Kerr | |
| 6,051,004 A | 4/2000 | Gill | |
| 6,527,767 B2 * | 3/2003 | Wang et al. | .................. 606/32 |
| 6,976,992 B2 | 12/2005 | Sachatello et al. | |
| 2009/0163950 A1 | 6/2009 | Waldman | |

FOREIGN PATENT DOCUMENTS

CN    2577776 Y    10/2003

OTHER PUBLICATIONS

"The Laschal Precision Suture Tome (PST)" (1 page).

* cited by examiner

*Primary Examiner* — Corrine M McDermott
*Assistant Examiner* — Robert A Lynch
(74) *Attorney, Agent, or Firm* — The Maxham Firm

(57) ABSTRACT

A surgical instrument having the dual functions of gripping a suture needle and cutting a suture. The instrument performs one function when the handles are pivoted together and the other function when the handles are pivoted apart. The instrument also provides for a precise suture tail length when the suture is cut.

9 Claims, 5 Drawing Sheets

NEEDLE HOLDER AND SUTURE CUTTER SURGICAL INSTRUMENT

FIELD OF THE INVENTION

This invention relates generally to surgical instruments, and more particularly to such an instrument configured to grip a surgical needle when closed, and to cut a suture when opened.

BACKGROUND

Needle holder instruments have long been available in the art, and used by surgeons and surgical team members. Such instruments facilitate surgical suture needle passage through tissue followed by suture knot tying and subsequent suture cutting required for ligating or tagging structures, closing surgical incisions and traumatic wounds, and any other surgical use requiring suturing. Typically a standard needle holder or driver and separate suture scissors have been necessary, requiring the user to switch between instruments (needle holder and scissors), or employ the use of an additional person or assistant to perform the act of suture cutting with scissors between the placement of individual sutures by the surgeon. Many attempts have been made to devise a dual-function instrument to reduce man-hours of work in the surgical field, reduce surgical suture time and, consequently, overall surgical case time.

Several of the known devices operate by closing the handles both to grip the needle and to cut the sutures. This requires careful timing and placement of the suture to be sure it is not cut too early in the operational process, and that the nose of the jaws does not damage the surrounding tissue. Other known devices include a third element as part of the instrument to function for cutting purposes. Some such dual function devices are relatively complex and difficult to maneuver in the tight confines of a surgical procedure. Some commercially available instruments suffer from one or both of the two major deficiencies inferred above. One such deficiency is the potential for inadvertent premature cutting of the suture during the act of suturing. Another is the potential to damage tissue with the distal needle holder tip of the instrument when cutting the suture in the more proximal scissors structure of the device.

The problem of inadvertent premature cutting of the suture has been recognized and U.S. Pat. No. 4,271,838 discloses a modified needle holder having a modified tip with a protected cutting mechanism and a slot in which to capture and cut the suture. This structure moves the cutting mechanism toward the tip of the instrument, improving accuracy, but still incompletely prevents the most distal needle holder tip from damaging tissue when the instrument is closed during the suture cutting process. Additionally, the cutting blade may be prone to catching tissue or suture material during the act of suturing. It is significant that the cutting mechanism of the instrument shown in the '838 patent is actuated by closing the handles and jaws of the instrument, as is true of most pivoted instruments.

SUMMARY OF EMBODIMENTS OF THE INVENTION

Broadly speaking, what is disclosed herein in various embodiments is a forceps-type instrument configured with arms formed with handles on one side of a pivot and needle gripping jaws on the opposite side of the pivot. As is conventional with instruments of this type, opposing moveable jaws close when the handles of the instrument are closed. Outside of the facing jaws are a slot and a cutting mechanism that functions completely separately from the gripping function while being manipulated by the same handles.

In the embodiments shown and discussed, when the jaws are operative to grip something, such as a suture needle, the cutting mechanism is not operable because the slot to receive the suture is blocked. When it is desired to cut a suture, the jaws must be disengaged from gripping the needle and then fully, or nearly fully, closed, which opens the suture cutting slot. When the suture is slid into the cutting slot, the handles are opened or spread, the jaws are commensurately spread, and suture cutting then occurs.

Among the advantages of the structure are that cutting action cannot be inadvertent, and when a suture is cut, tissue or other unintended material cannot be gripped or cut, because the jaws are closed to allow the suture to be inserted into the cutting slot and are then opened during the cutting process. Because the jaws must be at least nearly fully closed to enable the suture to be loaded into the slot to be cut, inadvertent cutting or crushing of tissues distal to the cutting mechanism is prevented. Further, when a needle is loaded between the jaws, the cutting slot is closed or nearly closed so the slot is unable to then capture the suture.

Another function of an embodiment of the invention is when a suture is cut, a uniform length of suture tail extends from the tied knot, effectively improving the integrity of the suture knot.

The description herein is directed to an instrument for gripping a suture and a suture needle, as well as for cutting a suture. It should be understood that the instrument can grip anything appropriate and can cut any type of strand that can fit into the cutting slot.

BRIEF DESCRIPTION OF THE DRAWING

The objects, advantages, and features of the invention, as evidenced by the embodiments shown and described, will be readily perceived from the following detailed description when read in conjunction with the accompanying drawing, in which:

FIG. 6A is an enlarged view of the jaws with sectional cutting planes there through;

DETAILED DESCRIPTION OF EMBODIMENTS OF THE INVENTION

Figure 1:
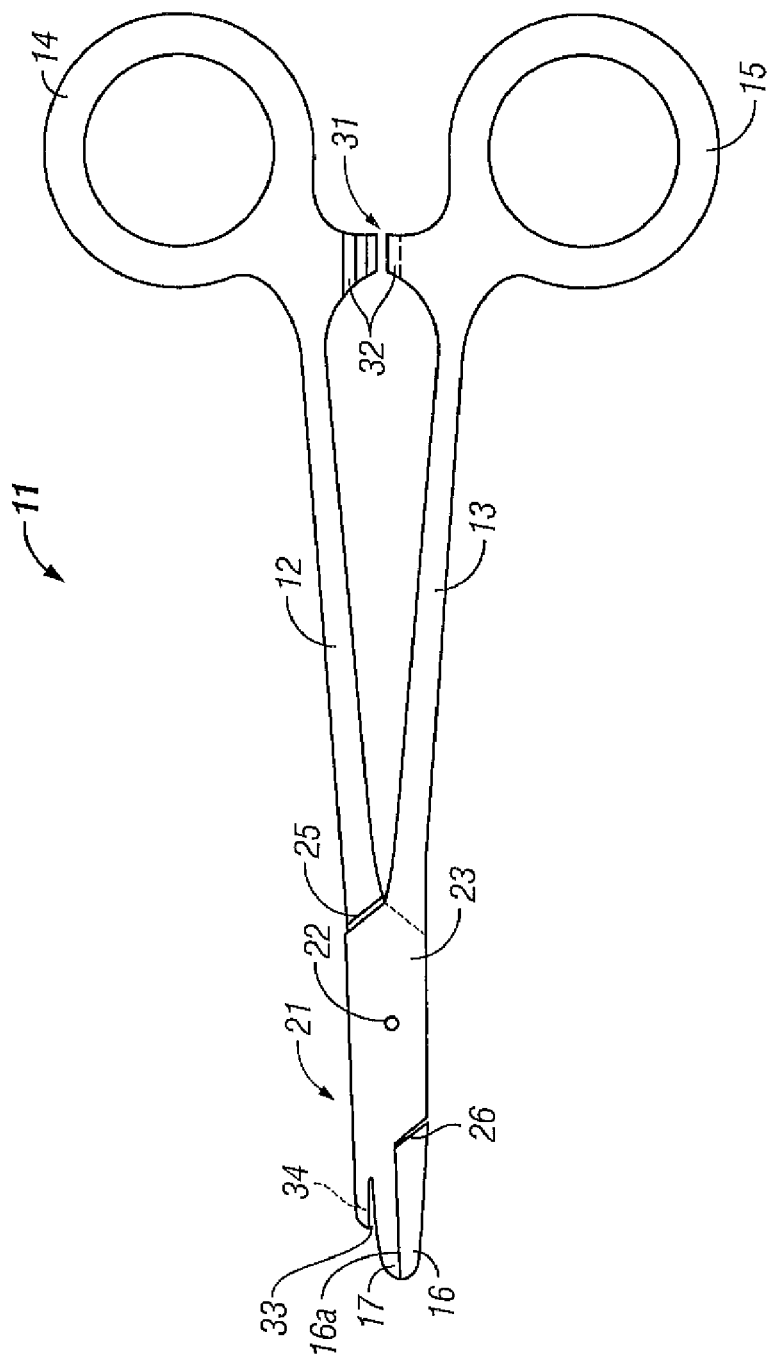
FIG. 1 is a plan view of an instrument constructed in accordance with the invention.
Figure 2:
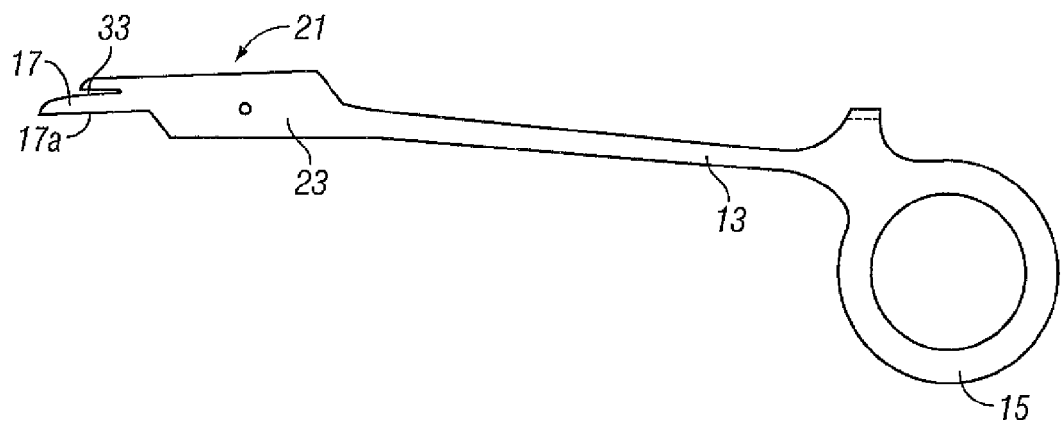
FIG. 2 is a plan view of a first arm of the instrument of FIG. 1.
Figure 3:
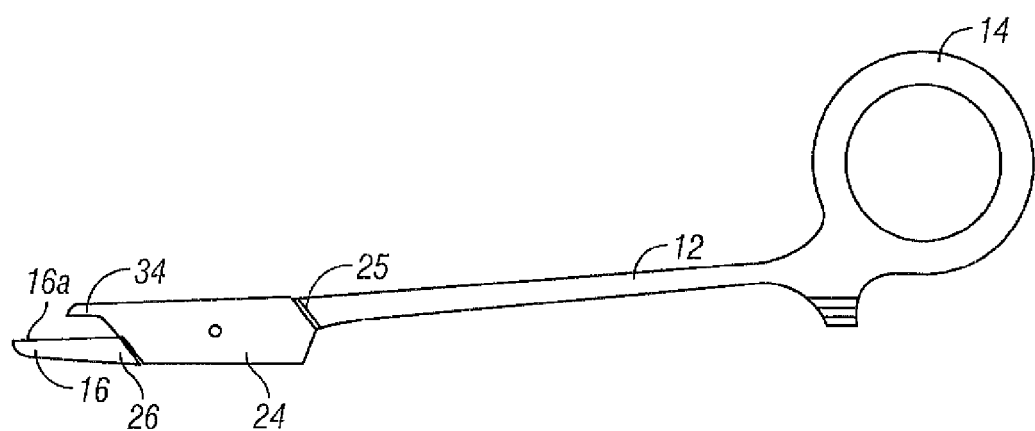
FIG. 3 is a plan view of the second arm of the instrument of FIG. 1.

With reference now to the drawing and more particularly to FIGS. 1-3 thereof, instrument 11 is shown with arms 12 and 13, having proximal handle ends 14 and 15, respectively, and distal jaws 16 and 17, respectively. Pivot mechanism typically comprises conventional box hinge 21 having pivot pin 22. The external box-shaped part of hinge 21 is designated with reference numeral 23 which is formed intermediate the ends of arm 13. Internal flat portion 24 is formed on arm 12 (shown in FIGS. 3 and 4) which is captured in box-shaped element 23. The portions 25, 26 of arm 12 immediately adjacent to element 23 are thicker than is the opening through element 23 so the flat part of arm 12 is captured within the box-shaped element. The box hinge prevents any wobbling or lateral play during pivoting of the arms with respect to each other and is a standard structure that has been used in surgical instruments for a long time.

This type of instrument is typically formed with a releasable ratchet locking arrangement 31 comprised of matching teeth 32 which engage and hold the jaws together when they are clamped tightly onto something, such as a suture needle. They are releasable by merely manipulating the handles to laterally separate them, as is well known in the medical field. This ratchet locking arrangement is not a requirement for this instrument and it can be provided as an alternative embodiment.

The following general description of the operative portion of the jaws will be followed by structural details. The jaw portion of the first arm contains a cutting slot generally parallel to the needle-gripping surface. This cutting slot begins proximal, or just rearwardly with respect to the tip of the jaw and extends for a distance toward the hinge. This jaw portion also contains a central slot perpendicular to the needle-gripping surface. This perpendicular slot extends through the depth of the jaw portion, beginning just rearwardly from the beginning of the cutting slot and is formed with an internal cutting edge. It is through this slot that the cutting blade attached to the second arm of the instrument is free to move during actuation of the instrument.

The jaw portion of the second arm contains a central cutting blade beginning rearwardly of the needle-gripping surface. The cutting blade moves within the central slot of the jaw portion of the first arm.

Figure 4:
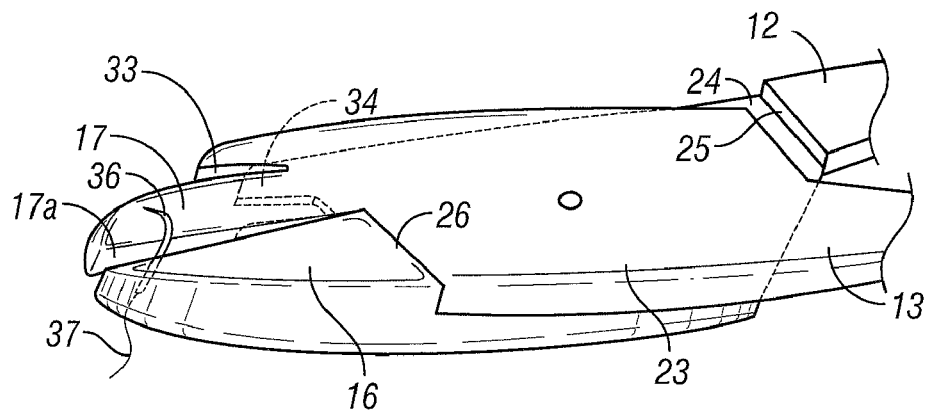
FIG. 4 is an enlarged perspective view of the jaws of the instrument of FIG. 1 in a gripping condition engaging a needle.
Figure 5:
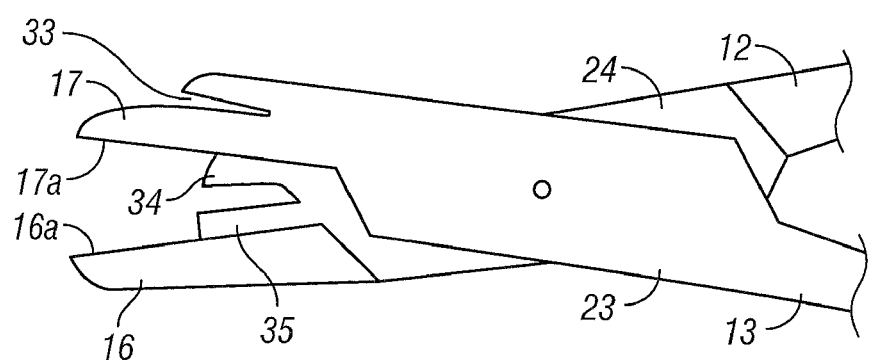
FIG. 5 is an enlarged view of the jaws of the instrument of FIG. 1 in an open condition for expository purposes.

The instrument jaws are shown in FIG. 1, and in more operational detail in FIGS. 4-6. Suture cutting slot 33 is shown open in FIG. 1, with jaws 16 and 17 nearly or fully closed together. The operative edge of cutting blade 34 is part of arm 12 and is laterally spaced from and somewhat or generally parallel to face 16a of jaw 16. By "somewhat or generally parallel" is meant that the angle of blade 34 with respect to jaw face 16a depends upon the size and shape of the instrument and the jaws themselves. It is the functioning of the blade with respect to jaw opening and closing that is the focus, rather than any particular angle. The surfaces 16a, 17a of the jaws can be any type that facilitates gripping a suture or needle. They may be smooth, toothed, knurled, or textured, for example, or they may be a combination of any functionally effective surfaces. The portions of the two jaws toward the hinge from the distal ends are unique and dissimilar, as is evident from this description.

FIGS. 5 and 6 also show blade guard 35, which is optional and which will be described below.

With reference now to FIG. 4, jaws 16 and 17 are closed upon suture needle 36, leaving the jaws slightly apart. Suture strand 37 is shown extending from the base of the needle. The jaw structure, together with cutting slot 33 and blade 34, are so configured that when the jaws are clamped on an object, such as needle 36, neither a suture nor any other item of that nature can be inserted into slot 33. This prevents unintended cutting by means of blade 34 when the jaws are slightly separated as shown in FIG. 4. Cutting slot 33 is so narrow that it is unlikely that any tissue or other material would enter it even when the instrument jaws are closed together and not upon an object. The cutting operation will be described with respect to FIG. 6.

FIG. 5 shows the jaw and blade structures with the handles, and thus the jaws, wide open, a position they can attain but would not likely be in when in use. This more clearly shows slot 33 in the distal end of arm 13, and blade 34 opposite jaw face 16a on the distal end of arm 12. Optional blade guard 35 is evident, projecting above face 16a toward blade 34. The blade guard prevents full exposure of blade 34 when the jaws are wide apart. This element is not essential to the proper functioning of the instrument.

Figure 6A:
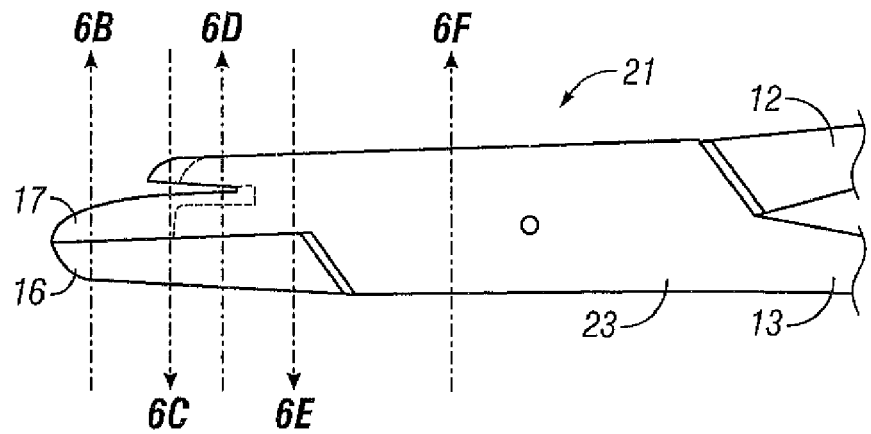

With reference now to FIG. 6, FIG. 6A shows the distal end of the instrument with the jaws closed together and slot 33 fully open. Several sectional views are provided to enhance the understanding of jaws/blade arrangement and how they function. It is not a requirement that the jaws be actually touching each other to provide access to the cutting slot, but they must be very nearly together.

Figure 6B:
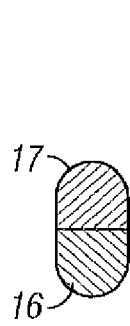
FIG. 6B is a cross section through cutting plane 6B in FIG. 6A.
Figure 6C:
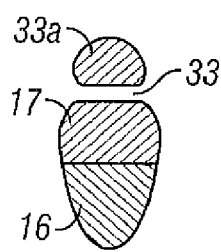
FIG. 6C is a cross section through cutting plane 6C in FIG. 6A.

FIG. 6B is a section through the jaw tips, just rearward of their distal ends. FIG. 6C is a section through the jaws somewhat toward hinge 21 from the tips, showing the opening of cutting slot 33. FIG. 6E is a section at the distal end of hinge 21 and FIG. 6F is a section through the box hinge.

Figure 6D:
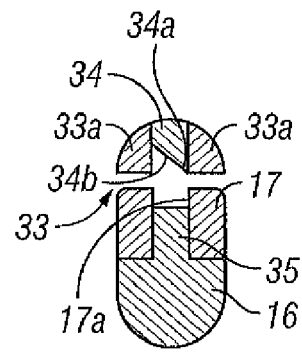
FIG. 6D is a cross section through cutting plane 6D in FIG. 6A.
Figure 6E:
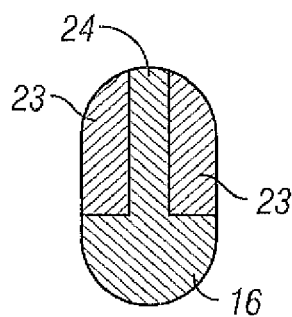
FIG. 6E is a cross section through cutting plane 6E in FIG. 6A.
Figure 6F:
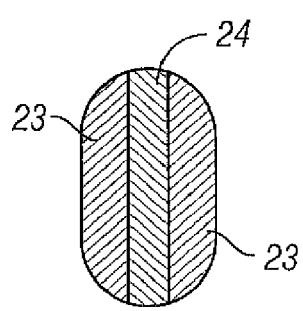
FIG. 6F is a cross section through cutting plane 6F in FIG. 6A.

FIG. 6D shows details of the cutting mechanism of the instrument. Cutting blade 34 on arm 12 has sharp edge 34a formed by bevelled surface 34b. The opposite cutting edge or surface is 17b on arm 13. As the jaws are opened slightly, cutting edge 34a moves downwardly to produce a cutting function with edge 17b of jaw 17.

To reiterate, as shown in FIG. 4, with the jaws slightly apart, the distal end of blade 34 blocks the entrance to slot 33 so that a suture, tissue, or other material cannot enter the slot and be subject to being cut by blade 34. Thus, inadvertent cutting of a suture or doing damage to tissue is highly unlikely. With reference to FIG. 6A, slot 33 is fully open when the jaws are closed together to admit a suture for cutting. Merely spreading handles 14, 15 relatively slightly will result in the suture within slot 33 being cut. For purposes of definition, the "cutting slot" is that portion rearward of the entrance to slot 33 that is between cutting blade 34 and cutting edge 17b. The jaws and the cutting slot are dimensioned so that when the jaws grip a suture needle, the cutting slot is blocked. In other words, when the jaws grip an object that is about the same thickness as the width of the cutting slot, the cutting blade substantially blocks entrance to the cutting slot for any strand of material that could otherwise be cut.

As an example of using the instrument constructed in accordance with embodiments of this invention, the needle gripping portions of the instrument are clamped around a needle or suture by bringing the loops of the two handle portions of the instrument into proximity. Further pressure on the loops actuates lock mechanism 31 of the instrument. The lock mechanism can be deactuated at any time by gentle pressure on the two handle portions while simultaneously applying a slight lateral pressure, and then separating the two handle portions. The instrument is utilized to pass the clamped needle and attached suture through the tissue. A surgical knot is then tied and either one or both of the suture ends is selected for cutting.

Figure 7:
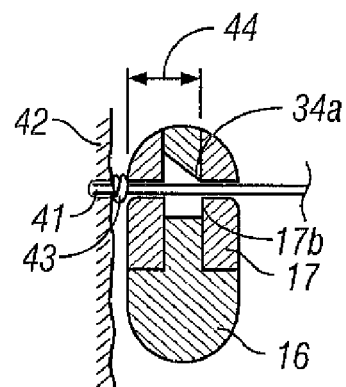
FIG. 7 is an enlarged partial section, similar to FIG. 6D, showing a suture in relation to tissue just prior to being cut.

With the handles and, consequently, the jaws of the instrument in a fully closed position, the instrument is advanced toward the suture end requiring cutting. The suture end is captured within the cutting slot in the distal jaw of arm 13, and the instrument is slid laterally down to the knot. The size of cutting slot 33 normally prevents the knot from entering, and facilitates uniform cutting of the suture above the knot. FIG. 7 shows how the instrument provides a uniform length suture tail when the suture is cut. Suture 41 is in tissue 42 and surgical knot 43 external to the tissue has been tied. When instrument 11 is placed in position to cut the suture material outside of the tissue, a length 44 of the suture tail is defined.

Figure 8A:
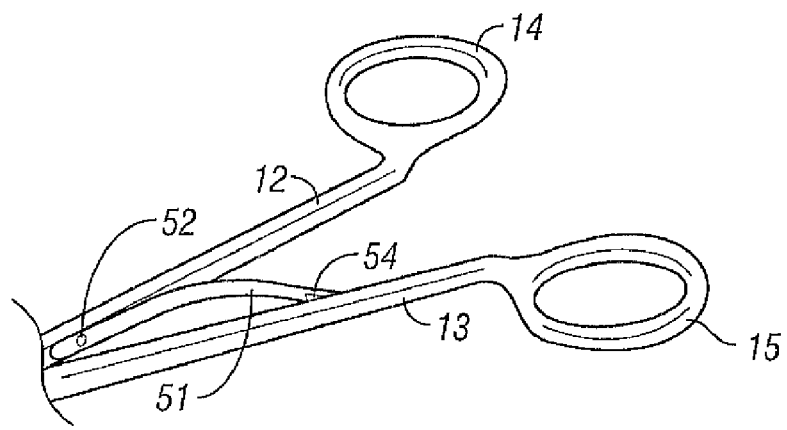
FIG. 8A shows the instrument handles with an optional biasing spring.
Figure 8B:
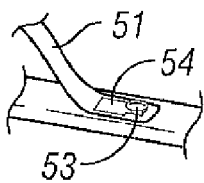
FIG. 8B is a partial view of an operative portion of FIG. 8A, showing how the optional biasing spring limits spreading of the handles.

An alternative embodiment is shown in FIG. 8. Surgical instruments of the forceps-type are often fitted with a spring which biases the handle apart but limits the distance they can be spread. As shown in FIG. 8A, spring element 51 is secured by appropriate means, such as welding or by rivet 52, to arm 12. The other end of spring 51 is formed with a key hole shaped slot 54 which removably engages rivet 53 fixed to arm 13, clearly shown in FIG. 8B. The head of rivet 53 is larger than the narrow portion of slot 54 and smaller than the larger opening of the slot. If the arms need to be spread wide, such as for sterilizing, spring 51 can be disengaged from rivet 53. It should also be noted that the elements 51, 52, 53, and 54 are optional and are not essential to functioning of the instrument.

The instrument may be made in a variety of sizes to accommodate user friendliness and surgical need. The tip of the instrument where the needle is held may be modified in all dimensions (width, height, taper, curve, surface, among others) to accommodate surgical need.

What is claimed is:

1. A surgical instrument comprising:
    a first arm having a handle formed on a proximal end, and a first jaw element formed on a distal end;
    a second arm having a handle formed on a proximal end, and a second jaw element formed on a distal end;
    a pivot mechanism connecting said first and second arms at a point intermediate said proximal and distal ends of said first and second arms to define said first and second jaw elements as opposing jaw elements, whereby opening or spreading said handles opens said first and second jaw elements and closing said first and second jaw elements together enables them to grip an external object; and
    cutting means adjacent said first and second jaw elements, said cutting means comprising:
    a cutting blade on said first arm;
    a cutting edge arrangement on said second arm; and
    a cutting slot for receiving material to be cut, said cutting slot communicating with said cutting blade and said cutting edge;
    said cutting means being shaped and configured to cut the material placed in said cutting slot when said handles are spread apart.

2. The instrument of claim 1, wherein said cutting means is so configured that said cutting slot is open to receive the material to be cut only when said first and second jaw elements are at least very nearly together.

3. The instrument of claim 2, wherein said cutting slot is sufficiently open to receive the material to be cut in a position adjacent to said cutting blade only when said first and second jaws are in contact with each other.

4. The instrument of claim 1, and further comprising a blade guard on said first arm adjacent to and spaced from said cutting blade.

5. The instrument of claim 1, wherein said cutting means is shaped and configured so that said cutting slot is blocked when an object is gripped between said first and second jaws.

6. The instrument of claim 5, where when an object is gripped between said first and second jaws, said cutting blade occupies said cutting slot, thereby preventing the material from entering said cutting slot.

7. The instrument of claim 1, wherein said cutting slot is the area between said cutting blade and said cutting edge, there being an external opening leading into said cutting slot.

8. The instrument of claim 7, where the distance between said first and second jaws when gripping an object is substantially equal to the width of said cutting slot.

9. A method for cutting a strand of material with a needle holder surgical instrument having pivotably interconnected arms and comprising a first arm having a handle formed on a proximal end and a first jaw element formed on a distal end thereof, a second arm having a handle formed on a proximal end and a second jaw element formed on a distal end thereof, and a pivot mechanism connecting the first and second arms at a point intermediate the proximal and distal ends of the first and second arms to define the first and second jaw elements as opposing jaw elements, whereby opening or spreading the handles opens the first and second jaw elements and closing the handles toward each other enables the first and second jaw elements to grip an external object, the method comprising:
    forming a first slot generally parallel with and laterally spaced from the first jaw element at the distal end of the first arm;
    forming a blade with a cutting edge generally parallel with and laterally spaced from the second jaw element at the distal end of the second arm;
    forming a second slot generally parallel with and perpendicular to the first slot in the distal end of the first arm, the first and second slots being arranged to mutually intersect;
    forming a cutting edge on the second slot at the intersection of the first and second slot;
    arranging the blade to enter the second slot in a manner to engage the cutting edge;
    closing the jaws together;
    placing a strand of material in the first slot; and
    opening the jaws by spreading the handles, thereby cutting the strand of material by engagement of the blade and the cutting edge.

\* \* \* \* \*